US009739271B2

(12) United States Patent
Chang

(10) Patent No.: US 9,739,271 B2
(45) Date of Patent: Aug. 22, 2017

(54) AUTOMATIC DEPRESSURIZING PUMP

(71) Applicant: KOGE ELECTRONICS CO., LTD, New Taipei (TW)

(72) Inventor: Kun-Lin Chang, New Taipei (TW)

(73) Assignee: KOGE ELECTRONICS CO., LTD, New Taipei (TW)

( * ) Notice: Subject to any disclaimer, the term of this patent is extended or adjusted under 35 U.S.C. 154(b) by 472 days.

(21) Appl. No.: 14/142,652

(22) Filed: Dec. 27, 2013

(65) Prior Publication Data

US 2015/0118084 A1 Apr. 30, 2015

(30) Foreign Application Priority Data

Oct. 24, 2013 (TW) .............................. 102138499 A

(51) Int. Cl.
| | |
|---|---|
| *F04B 39/08* | (2006.01) |
| *F04B 39/10* | (2006.01) |
| *F04B 1/12* | (2006.01) |
| *F04B 1/14* | (2006.01) |
| *F04B 49/03* | (2006.01) |
| *A61B 5/0225* | (2006.01) |
| *A61B 5/022* | (2006.01) |

(52) U.S. Cl.
CPC ............ *F04B 39/108* (2013.01); *F04B 1/122* (2013.01); *F04B 1/141* (2013.01); *F04B 39/08* (2013.01); *F04B 49/03* (2013.01); *A61B 5/022* (2013.01); *A61B 5/02208* (2013.01)

(58) Field of Classification Search
CPC ...... F04B 1/122; F04B 1/141; F04B 27/1036; F04B 27/1081; F04B 39/108; F04B 39/08; F04B 49/03; A61B 5/022; A61B 5/02208; A61B 5/0225; A61B 5/0235

USPC ................................ 417/299, 306, 307, 440
See application file for complete search history.

(56) References Cited

U.S. PATENT DOCUMENTS

| | | | |
|---|---|---|---|
| 3,730,172 A * | 5/1973 | Buddecke .......... | A61B 5/02208 128/901 |
| 4,759,692 A | 7/1988 | Morse | |
| 6,382,928 B1 | 5/2002 | Chang | |

FOREIGN PATENT DOCUMENTS

| | | |
|---|---|---|
| CN | 2813927 Y | 9/2006 |
| CN | 202370781 U | 8/2012 |
| CN | 202954941 U | 5/2013 |
| CN | 203702502 U | 7/2014 |

(Continued)

OTHER PUBLICATIONS

Office Action for corresponding Chinese Patent Application No. 201310508323.7, 5 pp., (Apr. 27, 2016).

*Primary Examiner* — Philip Stimpert
(74) *Attorney, Agent, or Firm* — WPAT, PC

(57) ABSTRACT

An automatic depressurizing pump includes an air-generating unit and an airflow control unit. The air-generating unit has a first air intake hole. An air generated by the air-generating unit drives the air control unit so as to inhale or exhale airflows through the first air intake hole. The airflow control unit includes a valve base, a first valve, a second valve, a top cover, and a resilient member. The valve base includes an air output chamber and a pressure chamber. The resilient member includes a second air output hole and a depressurization valve. The second air output hole is communicated with the top of the air output chamber, and the depressurization valve hermetically covers on and fixes to the top of the pressure chamber.

3 Claims, 12 Drawing Sheets

(56) References Cited

FOREIGN PATENT DOCUMENTS

| | | | |
|---|---|---|---|
| DE | 102012105006 A1 | 12/2012 | |
| DE | 112009000908 B4 | 9/2013 | |
| EP | 2698107 A1 * | 2/2014 | ........... A61B 5/0235 |
| JP | 2004239096 A | 8/2004 | |
| JP | 2012172577 A * | 9/2012 | .............. F04B 45/04 |
| JP | 2012-217684 A | 11/2012 | |
| TW | 200732559 A | 9/2007 | |
| TW | M476206 A | 4/2014 | |
| WO | WO 2013/084909 A1 | 6/2013 | |
| WO | WO 2013/157304 A1 | 10/2013 | |

* cited by examiner

AUTOMATIC DEPRESSURIZING PUMP

RELATED APPLICATIONS

This application claims priority to Taiwan Application Serial Number 102138499, filed Oct. 24, 2013, which is herein incorporated by reference.

BACKGROUND

Technical Field

The present disclosure relates to an automatic depressurizing pump.

Description of Related Art

A conventional pump can merely used to either increase or decrease a pressure, but it cannot automatically depressurize after pressuring according to a user's need. For example, an electronic sphygmomanometer needs to automatically depressurizing after pressuring, or the user cannot take the electronic sphygmomanometer off after measuring the blood pressure. A conventional solution is to combine the pump and a solenoid valve. When a pressurizing process is finished, the solenoid valve is used to depressurize. However, the conventional solution increases an additional cost of the solenoid valve. Therefore, if the solenoid valve can be replaced, the cost can be reduced.

SUMMARY

The disclosure provides an automatic depressurizing pump includes an air-generating unit and an airflow control unit. The air-generating unit has a first air intake hole. An air generated by the air-generating unit drives the air control unit so as to inhale or exhale airflows through the first air intake hole. The airflow control unit includes a valve base, a first valve, a second valve, a top cover, and a resilient member. The valve base including an air output chamber and a pressure chamber. The bottom of the air output chamber has a first valve opening. The bottom of the pressure chamber includes a second valve opening. The first valve is located inside the air output chamber and covers on the first valve opening. The second valve is located inside the pressure chamber and covers on the second valve opening. The top cover has a first air output hole and a first depressurization opening. The first air output hole is communicated with the air output chamber, and the first depressurization opening is aligned with the pressure chamber. The resilient member is located between the top cover and the valve base. The resilient member includes a second air output hole and a depressurization valve. The second air output hole is communicated with the air output chamber, and the depressurization valve hermetically covers on the pressure chamber, so that the pressure chamber is not communicated with the first depressurization opening. When the air-generating unit drives the airflow control unit, the depressurization valve seals the first depressurization opening, and the air entering the first air intake hole is transmitted to the first air output hole by the airflow control unit. When the air-generating unit stops driving the airflow control unit, the pressure chamber leaks the air, so that the depressurization valve is recessed to form a first depressurization opening to be communicated with the air output chamber and the first depressurization opening.

In an embodiment of the present disclosure, the bottom of the pressure chamber includes a non-flat surface. The second valve covers on the non-flat surface and forms a leaking gap with the non-flat surface. When the air-generating unit stops driving the airflow control unit, the pressure chamber leaks the air to the second valve opening through the leaking gap.

In an embodiment of the present disclosure, the bottom of the pressure chamber includes a groove. The second valve covers on the groove. When the air-generating unit stops driving the airflow control unit, the pressure chamber leaks the air to the second valve opening through the groove.

In an embodiment of the present disclosure, the pressure chamber includes a channel communicated with the outside of the automatic depressurizing pump. When the air-generating unit stops driving the airflow control unit, the pressure chamber leaks the air through the channel.

In an embodiment of the present disclosure, the pressure chamber includes a channel communicated with the air output chamber. When the air-generating unit stops driving the airflow control unit, the pressure chamber leaks the air through the channel.

In an embodiment of the present disclosure, the pressure chamber includes a channel communicated with a piston unit. When the air-generating unit stops driving the airflow control unit, the pressure chamber leaks the air through the channel.

In an embodiment of the present disclosure, an inner diameter of the channel is smaller than an inner diameter of the first air output hole.

In an embodiment of the present disclosure, the depressurization valve further has a second depressurization opening located between the air output chamber and the first depressurization opening.

In an embodiment of the present disclosure, the air-generating unit includes a piston-retaining base, a piston unit, a motor, and a linkage. The piston-retaining base has a second air intake hole. The piston unit is fixed to the piston-retaining base. The piston unit includes a first piston, a second piston, and a third air intake hole. The third air intake hole is communicated with the second air intake hole. The linkage is connected with a rotary shaft of the motor.

In an embodiment of the present disclosure, the bottom of the second valve includes a groove. When the air-generating unit stops driving the airflow control unit, the pressure chamber leaks the air to the second valve opening through the groove.

Accordingly, the automatic depressurizing pump of the present disclosure is equipped with the pressure chamber and the resilient member. When the automatic depressurizing pump is in the pressurizing status, the first depressurization opening is sealed. When the automatic depressurizing pump in the depressurizing status, the first depressurization opening is unsealed to depressurize quickly. When the volume of the inflatable object is 100 cc, the automatic depressurizing pump can quickly and effectively depressurize the inflatable object within 2 seconds. For instance, when an electronic sphygmomanometer is allocated with the automatic depressurizing pump, a solenoid valve is unnecessarily used. Therefore, the cost of the electronic sphygmomanometer can be reduced, and the lift time of the electronic sphygmomanometer can be increased. The automatic depressurizing pump of the present disclosure can be adapted to any equipment that requires to depressurizing. The automatic depressurizing pump is not limited to the electronic sphygmomanometer for it is merely an example.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
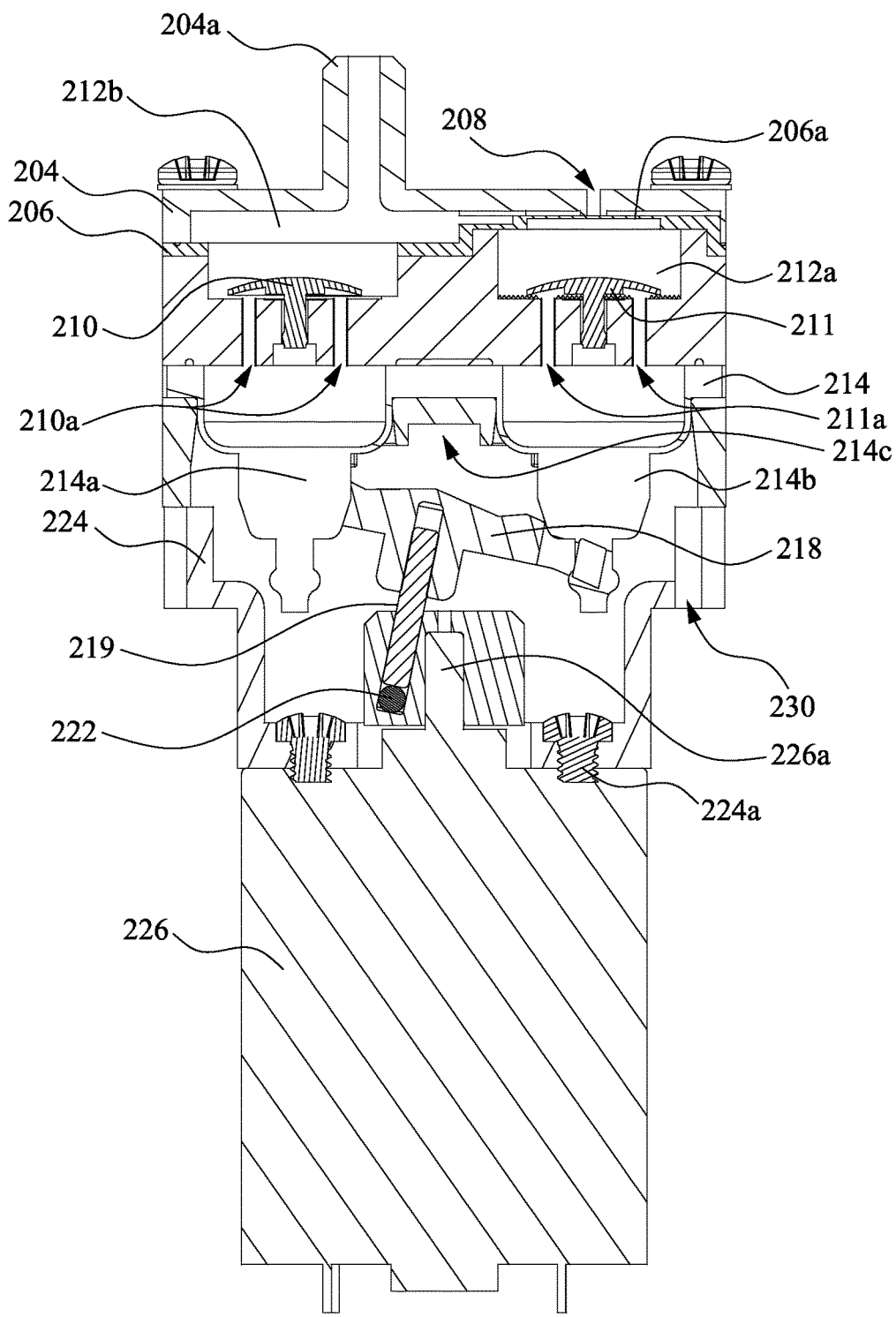
FIG. 1 is a cross-sectional view of an automatic depressurizing pump according to an embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

Figure 2:
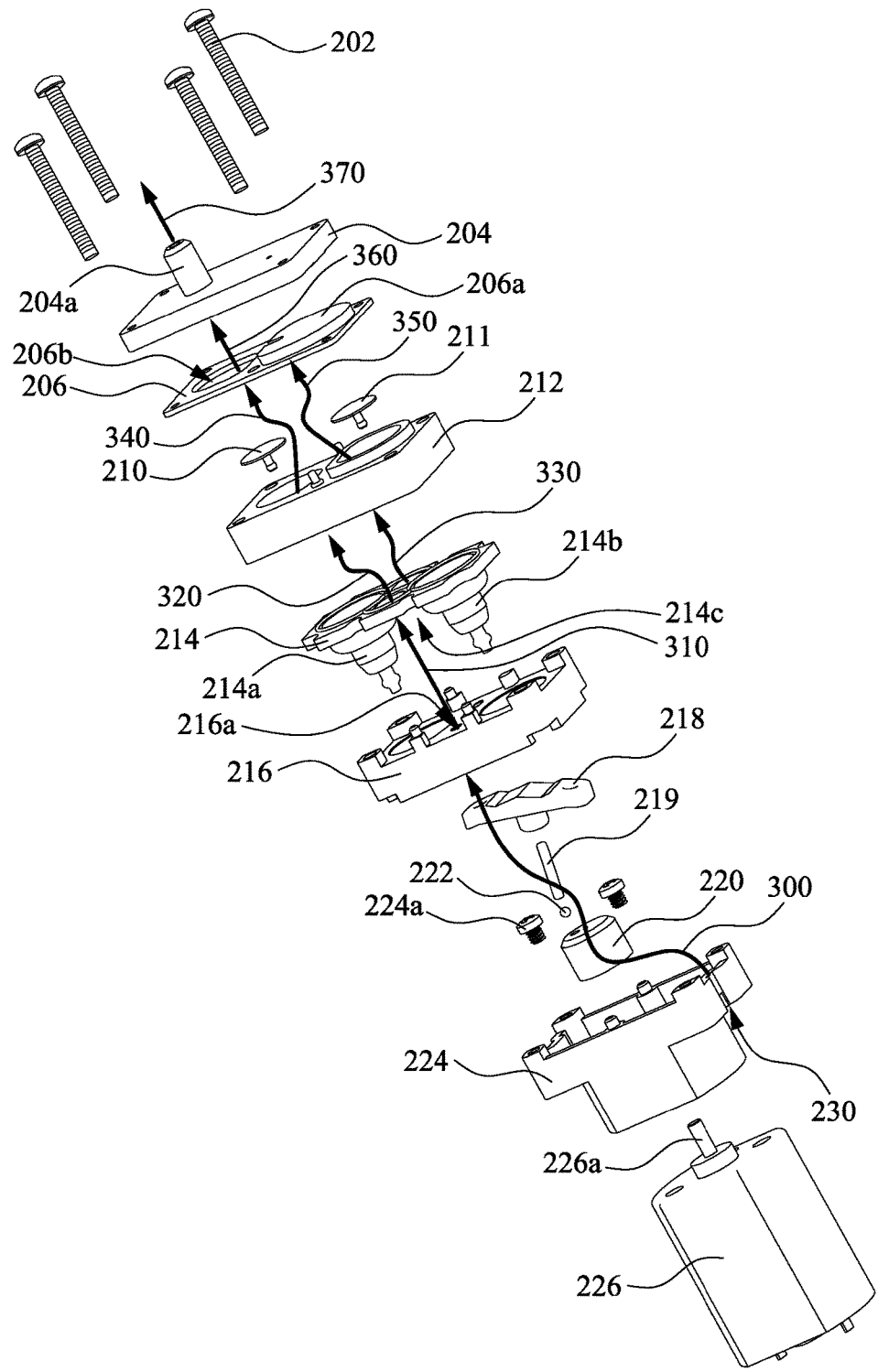
FIG. 2 is an exploded view of the automatic depressurizing pump according to an embodiment of the present disclosure.

In order to solve a problem that a conventional pump need an extra cost for a solenoid valve, the presented disclosure provides an automatic depressurizing pump to improve the problem. FIG. 1 is a cross-sectional view of the automatic depressurizing pump according to an embodiment of the present disclosure. FIG. 2 is an exploded view of the automatic depressurizing pump according to an embodiment of the present disclosure. The automatic depressurizing pump 200 includes an air-generating unit and an airflow control unit, and the air-generating unit and the airflow control unit are fixed by a plurality of screws 202. The air-generating unit includes a piston-retaining base 216, a piston unit 214, a motor 226, and a linkage 218. The piston-retaining base 216 has a second air intake hole 216a. The piston unit 214 is fixed to the piston-retaining base 216. The piston unit 214 has a first piston 214a, a second piston 214b, and a third air intake hole 214c. The third air intake hole 214c is communicated with the second air intake hole 216a. The linkage 218 is connected with the rotary shaft 226a of the motor 226. The air-generating unit has a first air intake hole 230. In an embodiment of the present disclosure, the motor 226 further includes a steel pin 219 and a steel ball 222 configured to reduce a friction force between the motor 226 and the linkage 218 during the operation of the motor 226. In an embodiment of the present disclosure, the motor 226 is fixed to a motor-retaining base 224 by a screw 224a, and is connected with an eccentric rotary shaft 220 through the motor-retaining base 224. The motor 226 controls the linkage 218 by the eccentric rotary shaft 220. The airflow control unit is driven by the air generated by the air-generating unit, so that the air passing through the first air intake hole 230 is inhaled into or exhaled out of the airflow control unit. The airflow control unit includes a valve base 212, a first valve 210, a second valve 211, a top cover 204, and a resilient member 206. The valve base 212 has an air output chamber 212b and a pressure chamber 212a. The bottom of the air output chamber 212b has a first valve opening 210a. The bottom of the pressure chamber 212a has a second valve opening 211a. The first valve opening 210a and the second valve opening 211a are respectively communicated with the first piston 214a and the second piston 214b. The first valve 210 is located inside the air output chamber 212b. The first valve 210 covers on the first valve opening 210a. The second valve 211 is located inside the pressure chamber 212a. The second valve 211 covers on the second valve opening 211a. The top cover 204 has a first air output hole 204a and a first depressurization opening 208. The first air output hole 204a is communicated with the air output chamber 212b. The first depressurization opening 208 is aligned with the pressure chamber 212a. The resilient member 206 is located between the top cover 204 and the valve base 212. The resilient member 206 has a second air output hole 206b and a depressurization valve 206a. The second air output hole 206b is communicated with the air output chamber 212b. The depressurization valve 206a hermetically covers on the pressure chamber 212a, so that the pressure chamber 212a is not communicated with the first depressurization opening 208. When the air-generating unit drives the airflow control unit, the air sequentially enters the first air intake hole 230, enters the airflow control unit along a direction 300, and then enters the second air intake hole 216a. The air passes through the third air intake hole 214c along a direction 310, and flows to the first piston 214a and the second piston 214b respectively along a direction 320 and a direction 330. The air that flows to the first piston 214a is compressed by the first piston 214a to sequentially pass through the first valve opening 210a, pass through the resilient member 206 along a direction 340, enter the first air output hole 204a along a direction 360, and finally be exhaled out of the first air output hole 204a along a direction 370. The air that flows to the second piston 214b is compressed by the second piston 214b to pass through the second valve opening 211a, form a pressure in the pressure chamber 212a, and press the depressurization valve 206a along a direction 350, so that the depressurization valve 206a seals the first depressurization opening 208, and thus the air does not leak from the first depressurization opening 208. An acting sequence and a theory of depressurizing processes are described below. In an embodiment of the present disclosure, the top cover 204 is a non-flexible member. In an embodiment of the present disclosure, the first piston 214a, the second piston 214b, the first valve 210, the second valve 211, and the resilient member 206 are made of rubber.

Figure 3:
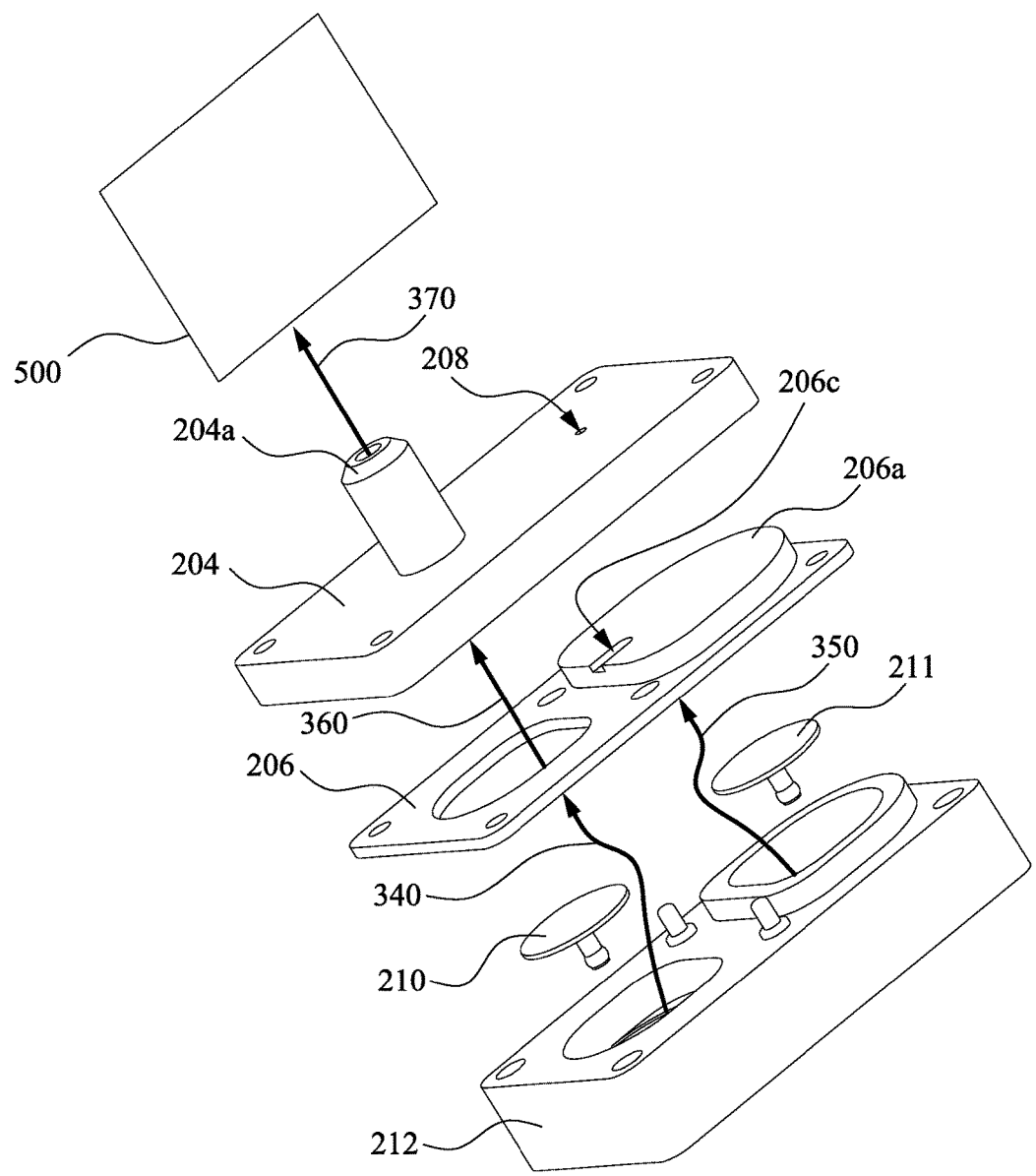
FIG. 3 is a partial exploded view of an airflow control unit according to an embodiment of the present disclosure.
Figure 4:
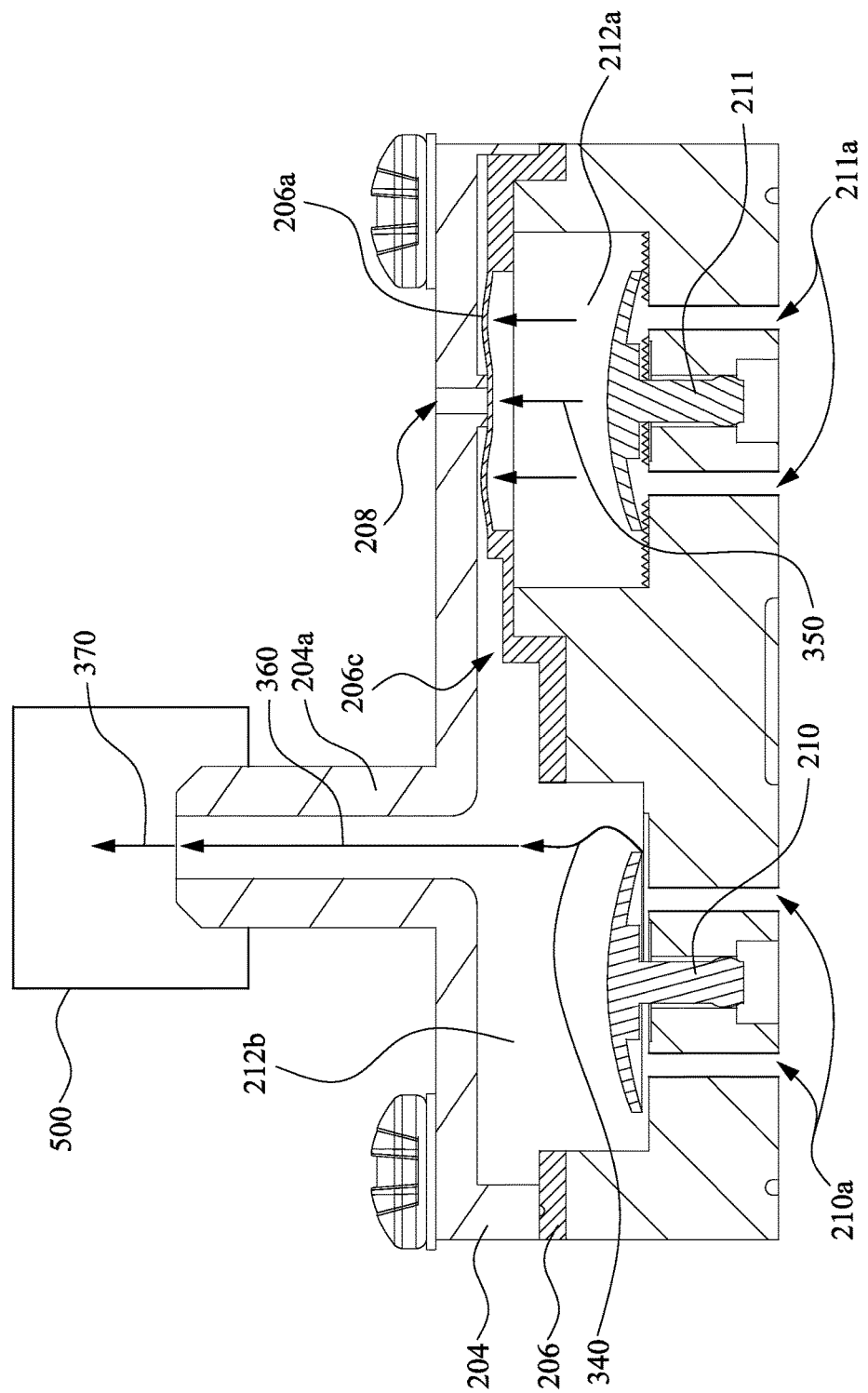
FIG. 4 is a partial cross-sectional view of the airflow control unit in an exhaling status according to an embodiment of the present disclosure.

FIG. 2 is an exploded view of the automatic depressurizing pump according to an embodiment of the present disclosure. FIG. 3 is a partial exploded view of the airflow control unit according to an embodiment of the present disclosure. FIG. 4 is a partial cross-sectional view of the airflow control unit in an exhaling status according to an embodiment of the present disclosure. When the air-generating unit drives the airflow control unit, the air enters the airflow control unit through the first air intake hole 230 and then enters the second air intake hole 216a along the direction 300. The air passes through the third air intake hole 214c along the direction 310, and flows to the first piston 214a and the second piston 214b respectively along the direction 320 and along the direction 330. The air that flows to the first piston 214a is compressed by the first piston 214a to sequentially pass through the first valve opening 210a, pass through the resilient member 206 along the direction 340, enter the first air output hole 204a along the direction 360, and finally be exhaled out of the first air output hole 204a along the direction 370 and flow to an inflatable object 500. The air that flows to the second piston 214b is compressed by the second piston 214b to pass through the second valve opening 211a, form a pressure in the pressure chamber 212a, and press the depressurization valve 206a along the direction 350, so that the depressurization valve 206a seals the first depressurization opening 208, and thus the air cannot leak from the first depressurization opening 208. According to another embodiment of the present disclosure, the first valve 210 and the second valve 211 are umbrella-shaped valves. According to another embodiment of the present disclosure, the depressurization valve 206a further includes a second depressurization opening 206c located between the air output chamber 212b and the first depressurization opening 208. Therefore, when the depressurization valve 206a is used to depressurize, the air can be leaked out of the first depressurization opening 208 more quickly, and the depressurization valve 206a is recessed more quickly. According to another embodiment of the present disclosure, a surface inside the air output chamber 212b that is covered by the first valve 210 is a polished surface, so that the first valve 210 can be hermetically sealed. According to another embodiment of the present disclosure, a working pressure of the automatic depressurizing pump 200 ranges from 0 to 400 mmHg. An acting sequence and a theory of the depressurizing processes are described below.

Figure 5:
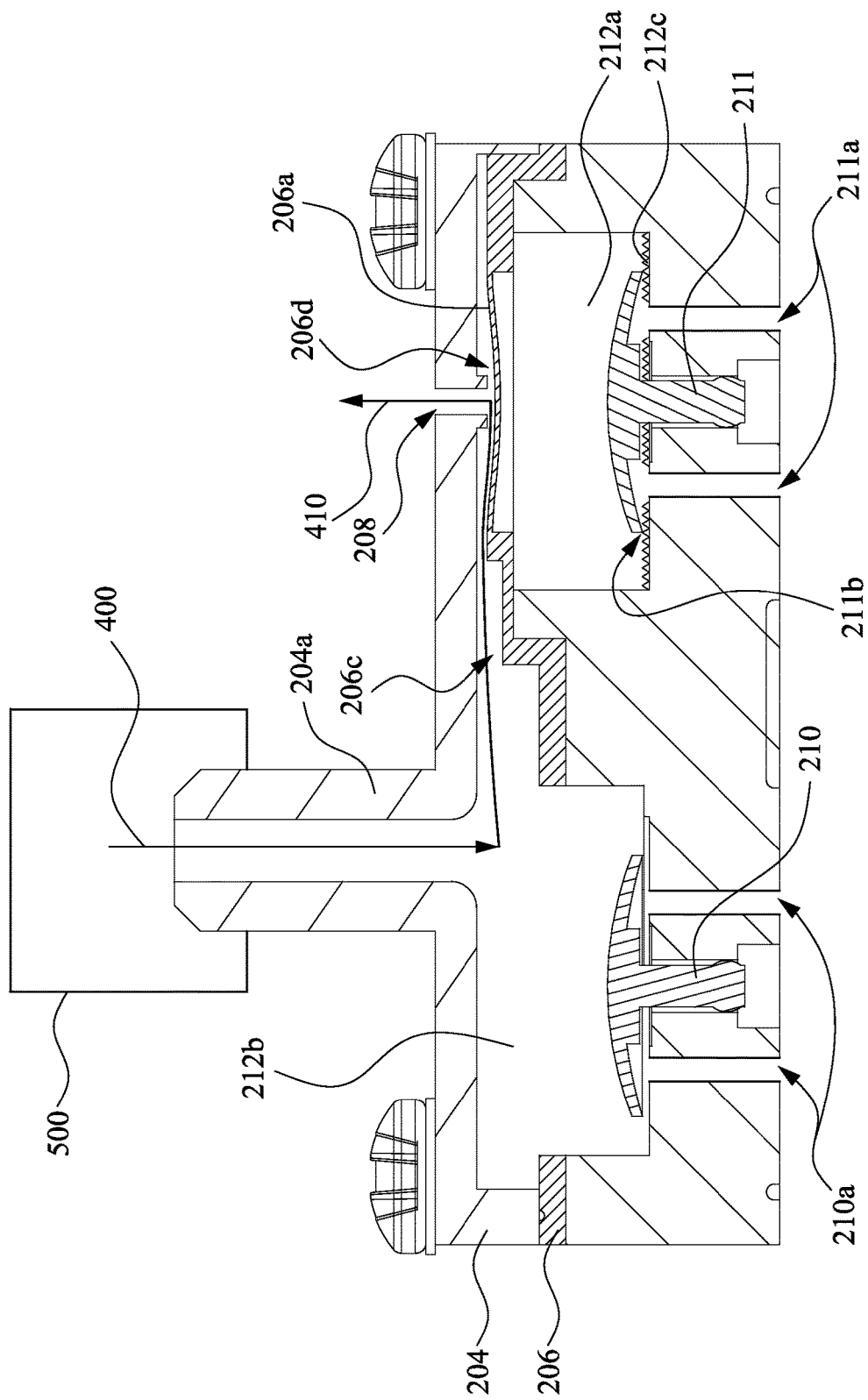
FIG. 5 is a partial cross-sectional view of the airflow control unit in a depressurizing status according to an embodiment of the present disclosure.

FIG. 5 is a partial cross-sectional view of the airflow control unit in a depressurizing status according to an embodiment of the present disclosure. The bottom of the pressure chamber 212a has a non-flat surface 212c. The second valve 211 covers on the non-flat surface 212c and forms a leaking gap 211b. When the air-generating unit stops driving the airflow control unit, the pressure chamber 212a leaks the air to the second valve opening 211a through the leaking gap 211b. The pressure chamber 212a leaks the air, so as to make the depressurization valve 206a be recessed to form a first depressurization opening 206d, and first depressurization opening 206d communicates the air output chamber 212b with the first depressurization opening 208. Therefore, the air passes through the first air output hole 204a along a direction 400 to enter the air output chamber 212b, passes through the first depressurization opening 206d along a direction 410, and is leaked from the first depressurization opening 208. In an embodiment of the present disclosure, a time for the automatic depressurizing pump to depressurize is within 2 seconds. In an embodiment of the present disclosure, the non-flat surface 212c is texture structure.

Figure 6:
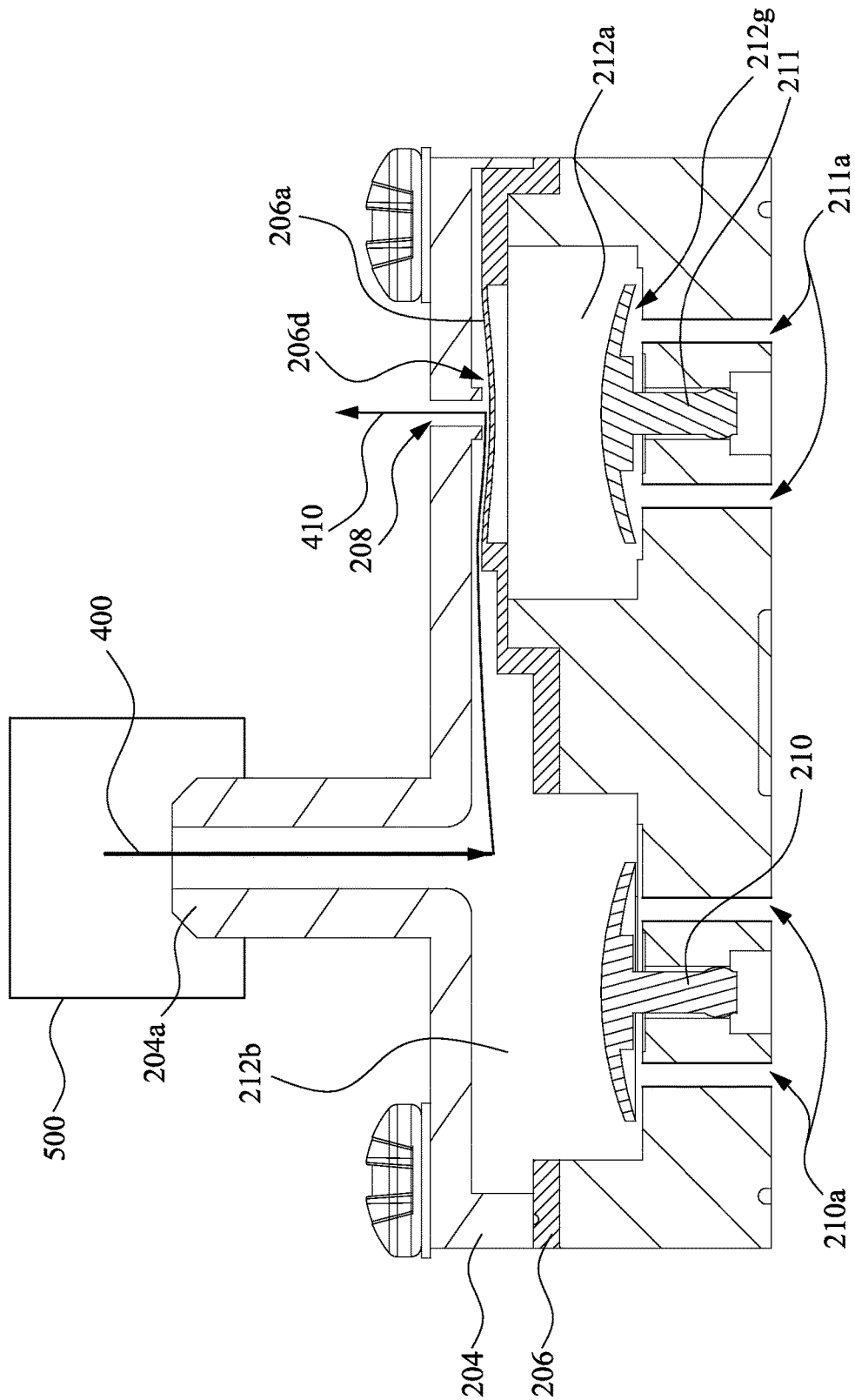
FIG. 6 is a partial cross-sectional view of an airflow control unit in the depressurizing status according to another embodiment of the present disclosure.

FIG. 6 is a partial cross-sectional view of an airflow control unit in the depressurizing status according to another embodiment of the present disclosure. The bottom of the pressure chamber 212a has a groove 212g. The second valve 211 covers on the groove 212g. When the air-generating unit stops driving the airflow control unit, the pressure chamber 212a leaks the air to the second valve opening 211a through the groove 212g. The pressure chamber 212a leaks the air to make the depressurization valve 206a be recessed to form a first depressurization opening 206d, and the first depressurization opening 206d communicates the air output chamber 212b with the first depressurization opening 208. Therefore, the air passes through the first air output hole 204a along a direction 400 to enter the air output chamber 212b, and then passes through the first depressurization opening 206d along a direction 410 to be leaked from the first depressurization opening 208.

Figure 7:
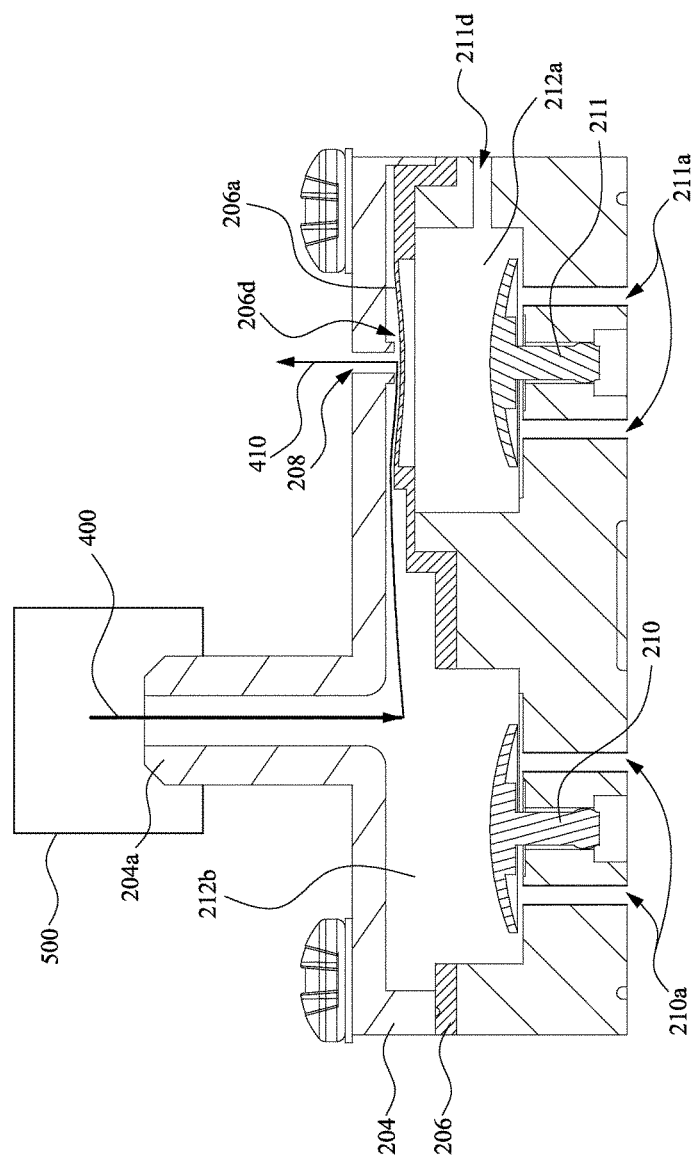
FIG. 7 is a partial cross-sectional view of an airflow control unit in the depressurizing status according to another embodiment of the present disclosure.

FIG. 7 is a partial cross-sectional view of an airflow control unit in the depressurizing status according to another embodiment of the present disclosure. The pressure chamber 212a has a channel 211d communicated with the outside of the automatic depressurizing pump 200. When the air-generating unit stops driving the airflow control unit, the pressure chamber 212a leaks the air through the channel 211d. The pressure chamber 212a leaks the air to make the depressurization valve 206a be recessed to form a first depressurization opening 206d and the first depressurization opening 206d communicates the air output chamber 212b with the first depressurization opening 208. Therefore, the air passes through the first air output hole 204a along a direction 400 to enter the air output chamber 212b, and then passes through the first depressurization opening 206d along a direction 410 to be leaked from the first depressurization opening 208.

Figure 8:
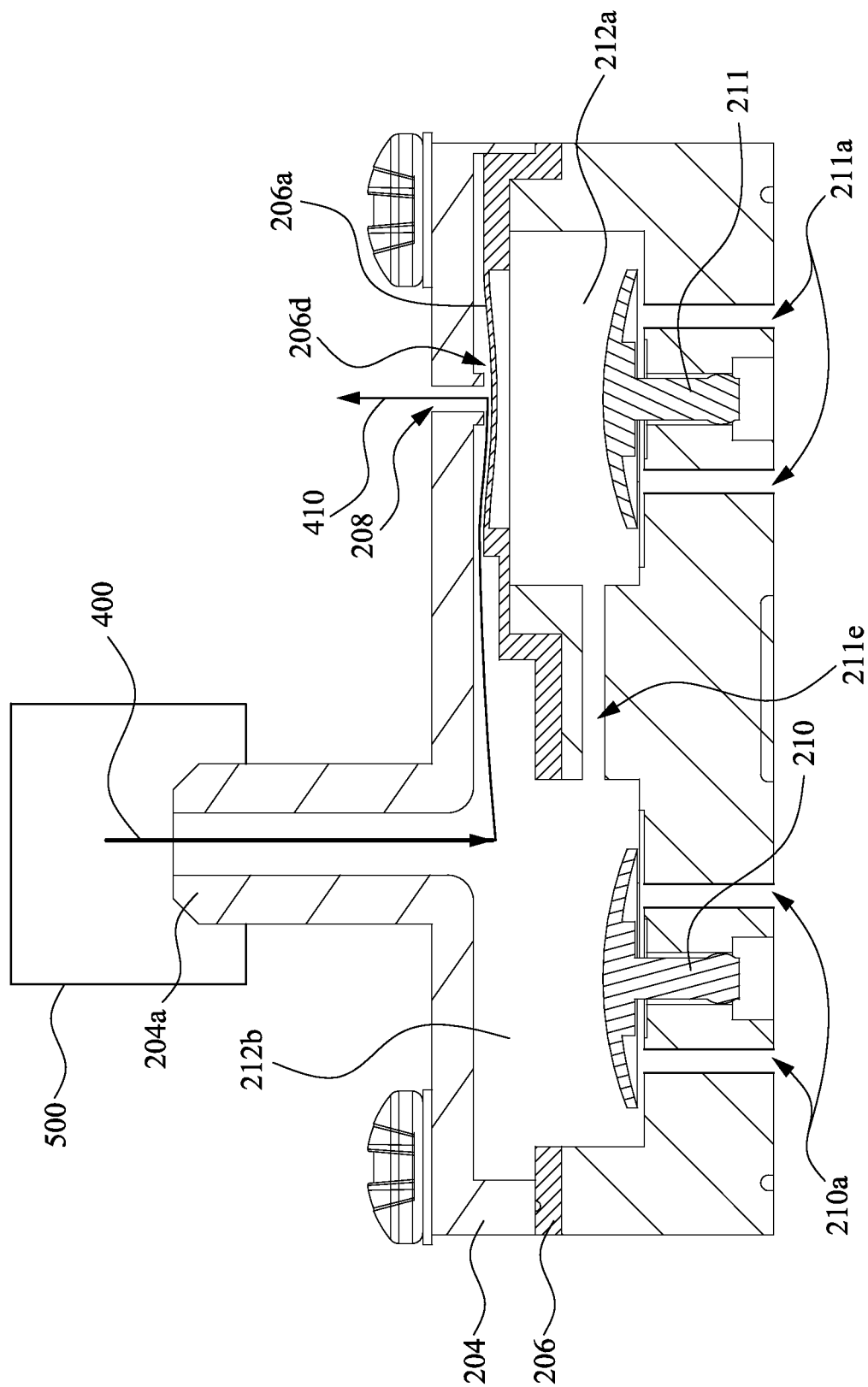
FIG. 8 is a partial cross-sectional view of an airflow control unit in the depressurizing status according to another embodiment of the present disclosure.

FIG. 8 is a partial cross-sectional view of an airflow control unit in the depressurizing status according to another embodiment of the present disclosure. The pressure chamber 212a has a channel 211e communicated with the air output chamber 212b. When the air-generating unit stops driving the airflow control unit, the pressure chamber 212a leaks the air through the channel 211e. The pressure chamber 212a leaks the air to make the depressurization valve 206a be recessed to form a first depressurization opening 206d, and the first depressurization opening 206d communicates the air output chamber 212b with the first depressurization opening 208. Therefore, the air passes through the first air output hole 204a along a direction 400 to enter the air output chamber 212b, and then passes through the first depressurization opening 206d along a direction 410 to be leaked from the first depressurization opening 208.

Figure 9:
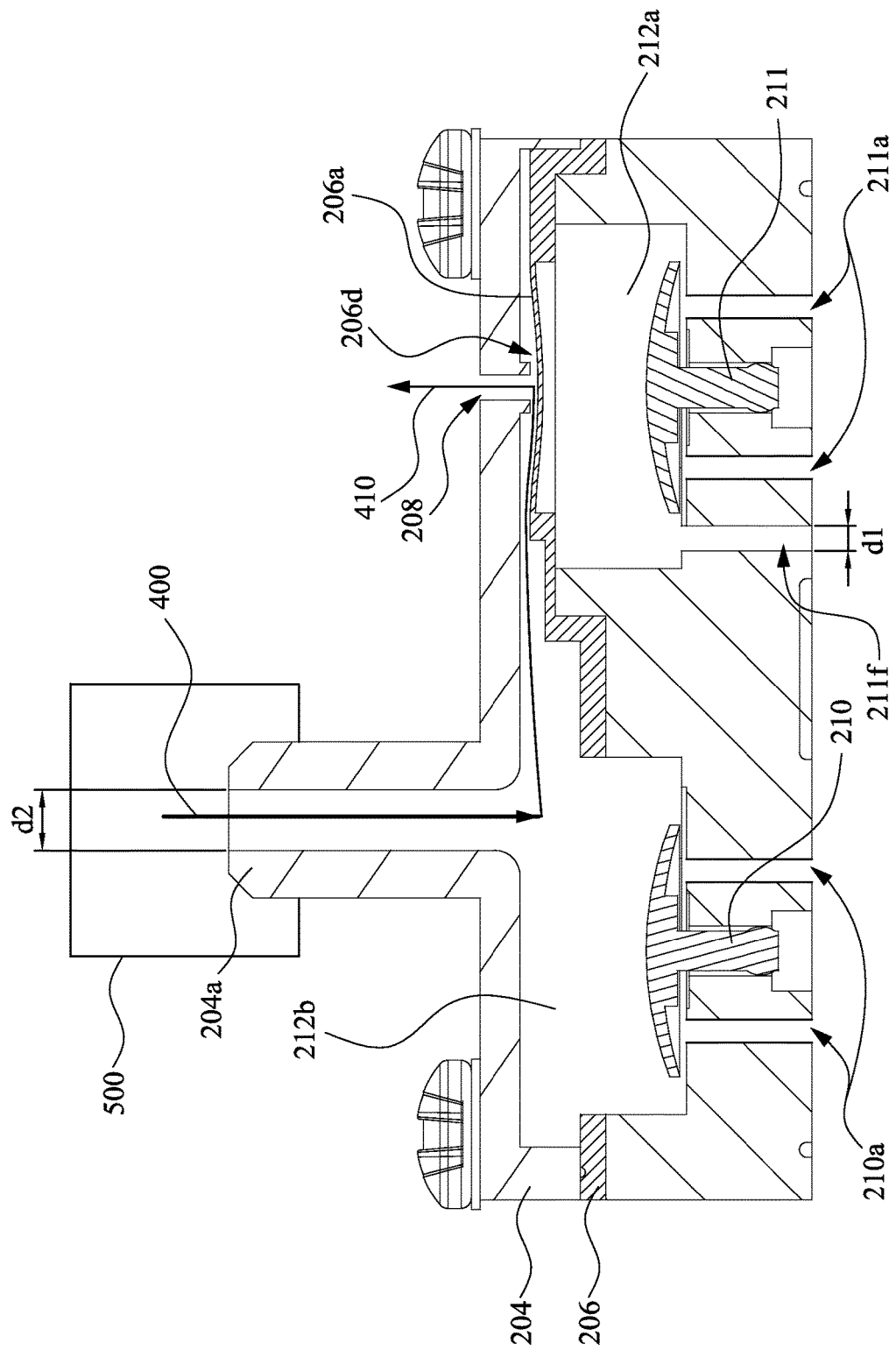
FIG. 9 is a partial cross-sectional view of an airflow control unit in the depressurizing status according to another embodiment of the present disclosure.

FIG. 9 is a partial cross-sectional view of an airflow control unit in the depressurizing status according to another embodiment of the present disclosure. The pressure chamber 212a has a channel 211f communicated with the piston unit 214 (referring to FIG. 2). When the air-generating unit stops driving the airflow control unit, the pressure chamber 212a leaks the air through the channel 211f. The pressure chamber 212a leaks the air to make the depressurization valve 206a be recessed to form a first depressurization opening 206d, and the depressurization valve 206a communicates the air output chamber 212b with the first depressurization opening 208. Therefore, the air passes through the first air output hole 204a along a direction 400 to enter the air output chamber 212b, and then passes through the first depressurization opening 206d along a direction 410 to be leaked from the first depressurization opening 208. According to another embodiment of the present disclosure, an inner diameter d1 of the channel is smaller than an inner diameter d2 of the first air output hole 204a.

Figure 10:
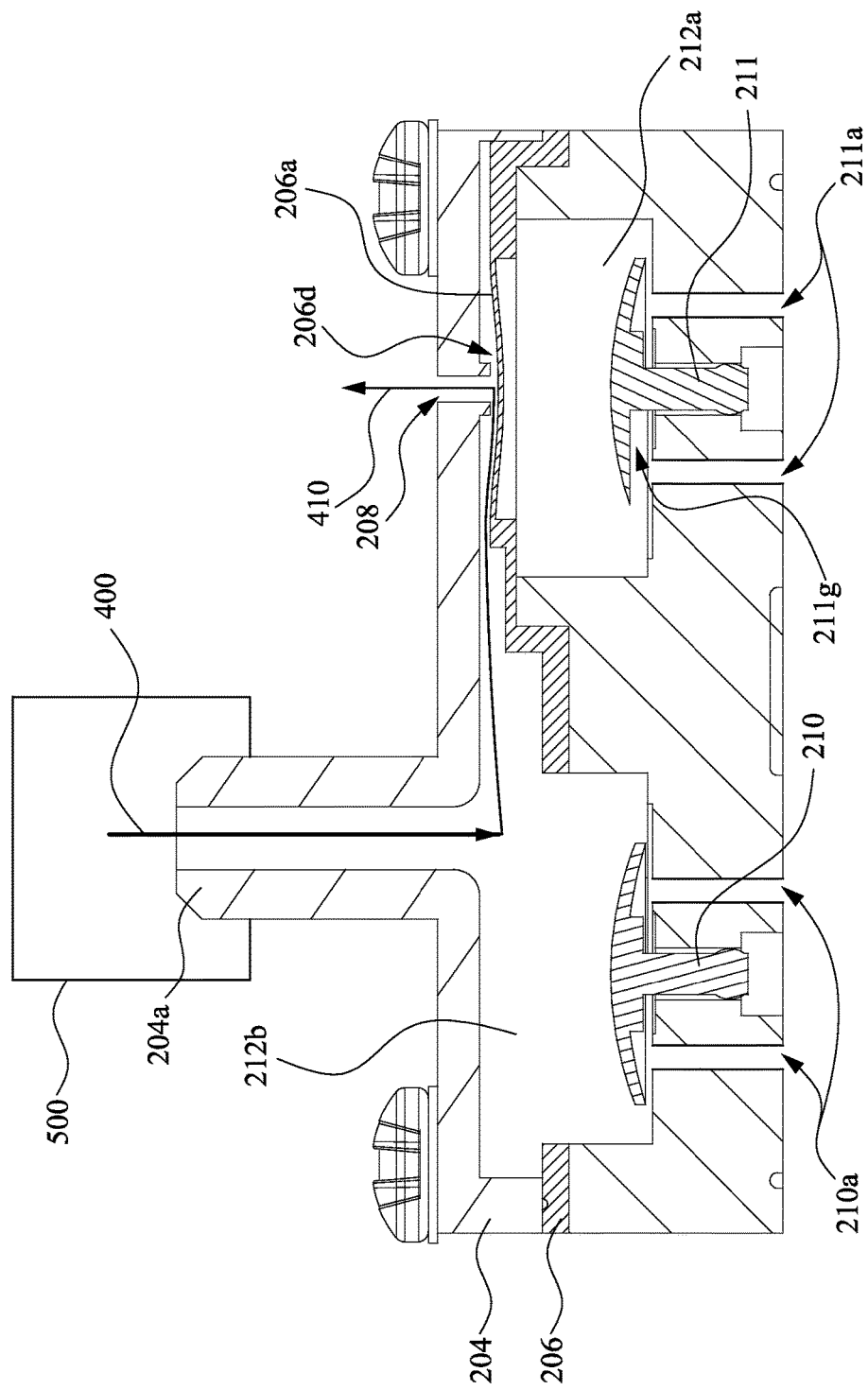
FIG. 10 is a partial cross-sectional view of an airflow control unit in the depressurizing status according to another embodiment of the present disclosure.

FIG. 10 is a partial cross-sectional view of an airflow control unit in the depressurizing status according to another embodiment of the present disclosure. The bottom of the second valve 211 has a groove 211g. When the air-generating unit stops driving the airflow control unit, the pressure chamber 212a leaks the air to the second valve opening 211a through the groove 211g. The pressure chamber 212a leaks the air to make the depressurization valve 206a be recessed to form a first depressurization opening 206d, and the depressurization valve 206a communicates the air output chamber 212b with the first depressurization opening 208. Therefore, the air passes through the first air output hole 204a along a direction 400 to enter the air output chamber 212b, and then passes through the first depressurization opening 206d along a direction 410 to be leaked from the first depressurization opening 208.

Figure 11:
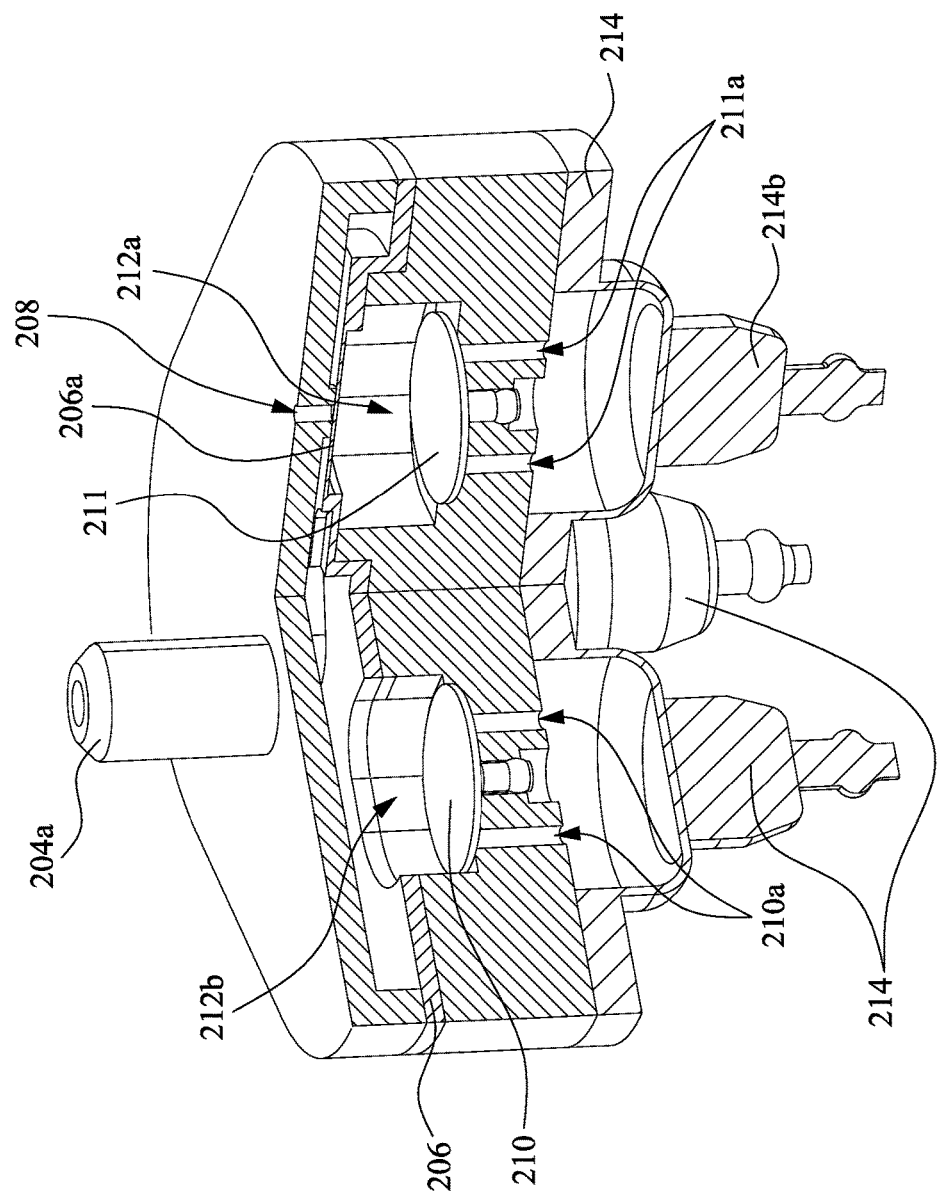
FIG. 11 is a partial cross-sectional view of the airflow control unit according to another embodiment of the present disclosure.
Figure 12:
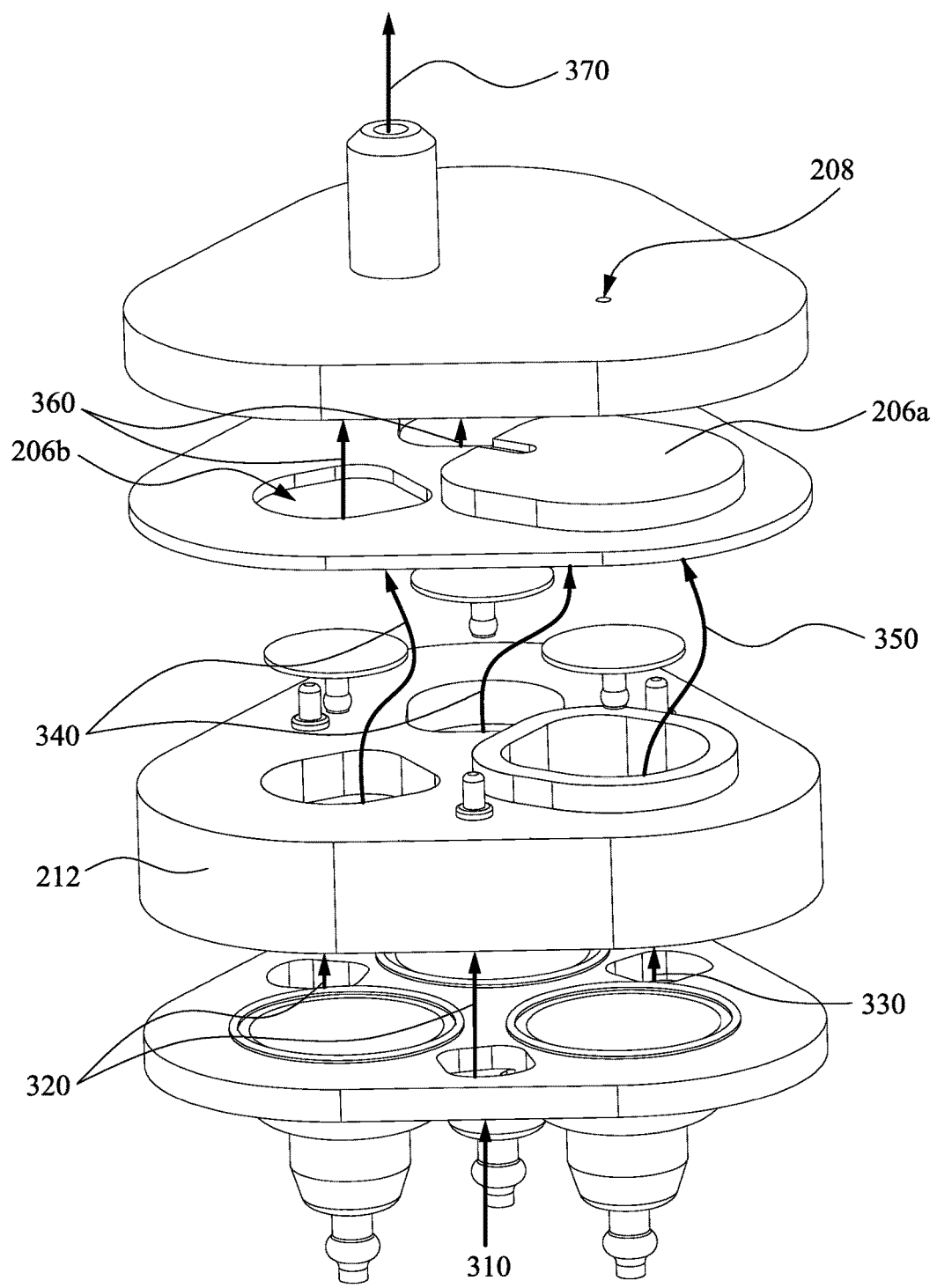
FIG. 12 is a partial exploded view of the airflow control unit according to another embodiment of the present disclosure.

FIG. 11 is a partial cross-sectional view of the airflow control unit according to another embodiment of the present disclosure. FIG. 12 is a partial exploded view of the airflow control unit according to another embodiment of the present disclosure. In the embodiment of the present disclosure, the same reference number indicates the same device and thus performs the same function, so they are not described again here. In this embodiment, the differences between FIG. 1 to FIG. 9 are as follows: the piston unit 214 has a plurality of the first pistons 214a; the valve base 212 has a plurality of the air output chambers 212b and a plurality of the first valve openings 210a; the airflow control unit has a plurality of the first valves 210; and the resilient member 206 has a plurality of the second air output holes 206b. According to another embodiment of the present disclosure, each of the devices is plural and can be modified to perform the same function. People having ordinary skill in the art can make proper modification to the quantity of the devices in the disclosure according to their actual needs.

Accordingly, the automatic depressurizing pump of the present disclosure is equipped with the pressure chamber and the resilient member. When the automatic depressurizing pump is in the pressurizing status, the first depressurization opening is sealed. When the automatic depressurizing pump in the depressurizing status, the first depressurization opening is unsealed to depressurize quickly. When the volume of the inflatable object is 100 cc, the automatic depressurizing pump can quickly and effectively depressurize the inflatable object within 2 seconds. For instance, when an electronic sphygmomanometer is allocated with the automatic depressurizing pump, a solenoid valve is unnecessarily used. Therefore, the cost of the electronic sphygmomanometer can be reduced, and the lift time of the electronic sphygmomanometer can be increased. The automatic depressurizing pump of the present disclosure can be adapted to any equipment that requires to depressurizing. The automatic depressurizing pump is not limited to the electronic sphygmomanometer for it is merely an example.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An automatic depressurizing pump, comprising:
   an air-generating unit having a first air intake hole; and
   an airflow control unit, wherein an air generated by the air-generating unit drives the air control unit so as to inhale or exhale airflows through the first air intake hole, and the airflow control unit comprises:
   a valve base comprising an air output chamber and a pressure chamber, a bottom side of the air output chamber having a first valve opening, a bottom side of the pressure chamber comprising a second valve opening;
   a first valve located inside the air output chamber and covering on the first valve opening;
   a second valve located inside the pressure chamber and covering on the second valve opening;
   a top cover having a first air output hole and a first depressurization opening, wherein the first air output hole is communicated with the air output chamber, and the first depressurization opening is aligned with a top opening of the pressure chamber; and
   a resilient member located between the top cover and the valve base, wherein the resilient member comprises a second air output hole and a depressurization valve, the second air output hole is communicated with a top opening of the air output chamber, and the depressurization valve hermetically covers on and fixes to the top opening of the pressure chamber, so that the pressure chamber is not communicated with the first depressurization opening, wherein a bottom side of the depressurization valve seals around an edge of the top opening of the pressure chamber;
   when the air-generating unit drives the airflow control unit, a top side of the depressurization valve seals the first depressurization opening, and the air entering the first air intake hole is transmitted to the first air output hole by the airflow control unit,
   wherein the air-generating unit comprises at least one first working chamber which provides a first flow of air to the air output chamber via a first path including the first valve and at least one second working chamber which provides a second flow of air to the pressure chamber via a second path including the second valve, wherein the first and the second paths are separated throughout their respective extents; and
   when the air-generating unit stops driving the airflow control unit, the pressure chamber leaks the air, so that the depressurization valve is recessed so that a second depressurization opening communicates with the air output chamber and the first depressurization opening, and the top side of the depressurization valve does not seal the first depressurization opening.

2. The automatic depressurizing pump of claim 1, wherein the pressure chamber comprises a channel communicated with an outside of the automatic depressurizing pump, and when the air-generating unit stops driving the airflow control unit, the pressure chamber leaks the air through the channel.

3. The automatic depressurizing pump of claim 2, wherein an inner diameter of the channel is smaller than an inner diameter of the first air output hole.

* * * * *